United States Patent [19]
Ouchi

[11] Patent Number: 6,134,467
[45] Date of Patent: Oct. 17, 2000

[54] DRAINAGE TUBE INTRODUCER FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/168,851

[22] Filed: Oct. 9, 1998

[30] Foreign Application Priority Data

| Oct. 29, 1997 | [JP] | Japan | 9-296784 |
| Nov. 10, 1997 | [JP] | Japan | 9-306710 |
| Jul. 23, 1998 | [JP] | Japan | 10-207293 |

[51] Int. Cl.$^7$ ............................ A61N 1/30; A61M 5/178; A61B 18/18
[52] U.S. Cl. ......................... 604/21; 604/164.01; 606/41
[58] Field of Search .................... 604/21, 22, 164.01, 604/164.03, 239, 272; 606/32, 34, 37–40, 45–49, 167, 170, 184, 185

[56] References Cited

U.S. PATENT DOCUMENTS

| 4,824,433 | 4/1989 | Marz et al. | 604/21 |
| 5,531,692 | 7/1996 | Rogers | 604/164.01 |
| 5,599,348 | 2/1997 | Gentelia et al. | 606/45 |
| 5,807,339 | 9/1998 | Bostrom et al. | 604/164.01 |
| 5,868,684 | 2/1999 | Akerfeldt et al. | 604/164.01 |
| 5,876,400 | 3/1999 | Songer | 606/45 |

FOREIGN PATENT DOCUMENTS

| 55-99941 | 6/1982 | Japan . |
| 9103433 | 4/1997 | Japan . |

*Primary Examiner*—Sharon Kennedy
*Attorney, Agent, or Firm*—Greenblum & Bernstein, P.L.C.

[57] ABSTRACT

A drainage tube introducer for an endoscope includes a flexible guide wire having at a distal end thereof a puncturing portion adapted to be stabbed into an organic tissue. A drainage tube is fitted on a portion of the guide wire that is closer to the distal end thereof. The drainage tube is held on the guide wire by frictional resistance. A flexible pusher is loosely fitted on the guide wire axially movably so that the drainage tube is pushed out forwardly by the pusher.

4 Claims, 5 Drawing Sheets

DRAINAGE TUBE INTRODUCER FOR ENDOSCOPE

BACKGROUND OF THE INVENTION

The present disclosure relates to subject matter contained in Japanese Patent Application No. 9-296784 (filed on Oct. 29, 1997), Japanese Patent Application No. 9-306710 (filed on Nov. 10, 1997), and Japanese Patent Application No. 10-207293 (filed on Jul. 23, 1998), which are expressly incorporated herein by reference in their entireties.

1. Field of the Invention

The present invention relates to a drainage tube introducer for an endoscope that is used through an instrument-inserting channel of the endoscope to introduce a drainage tube into a body cavity for the purpose of draining (through-draining) a narrow part in the body cavity.

2. Description of the Prior Art

To draw accumulated pancreatic juice from the pancreas or the pancreatic duct into the stomach, there is a technique whereby a drainage tube is introduced into the patient's body through an endoscope. According to the conventional procedure, a puncturing instrument that has a guide wire removably inserted therein is passed through an instrument-inserting channel of an endoscope (particularly, an ultrasonic endoscope), and the pancreas is pierced with the puncturing instrument from the inner wall of the stomach.

Thereafter, with the distal end of the guide wire left in the pancreatic duct, the puncturing instrument is drawn out of the patient's body. Then, a drainage tube is inserted into the pancreatic duct by passing it over the guide wire. Finally, the guide wire is drawn out of the patient's body, thereby allowing the drainage tube to be left under the conditions that one end of the drainage tube opens into the pancreatic duct, and the other end opens into the stomach.

A conventional puncturing instrument used in the above-described procedure has an inner tube that allows a guide wire to be removably inserted therein over the entire length of the inner tube. The inner tube has a tubular needle at the distal end thereof. The tubular needle has a syringe needle-like shape. The inner tube is axially movably inserted in a sheath that is removably inserted into an instrument-inserting channel of an endo scope.

As stated above, introduction of a drainage tube through an endoscope requires a troublesome operation in which after the tissue in a body cavity has been punctured, the puncturing instrument is drawn out, with the distal end of the guide wire left in the pancreatic duct. Then, the drainage tube is inserted into the pancreatic duct by passing it over the guide wire. In particular, it is very difficult and troublesome to draw out only the puncturing instrument by an operation conducted at the proximal end of the sheath while preventing the distal end of the guide wire from dislodging from the pancreatic duct.

SUMMARY OF THE INVENTION

An object of the present invention is to provide a drainage tube introducer whereby after the tissue in a body cavity has been punctured through an endoscope, a drainage tube can be readily introduced into the punctured part.

Other objects and advantages of the present invention will become apparent from the following detailed description of illustrated embodiments of the invention.

According to the present invention, there is provided a drainage tube introducer for an endoscope that includes a flexible guide wire having at a distal end thereof a puncturing portion adapted to be stabbed into an organic tissue. A drainage tube is fitted on a portion of the guide wire that is closer to the distal end thereof. The drainage tube is held on the guide wire by frictional resistance. A pusher is loosely fitted on the guide wire axially movably so that the drainage tube is pushed out forwardly by the pusher. The pusher is formed from a flexible tube.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
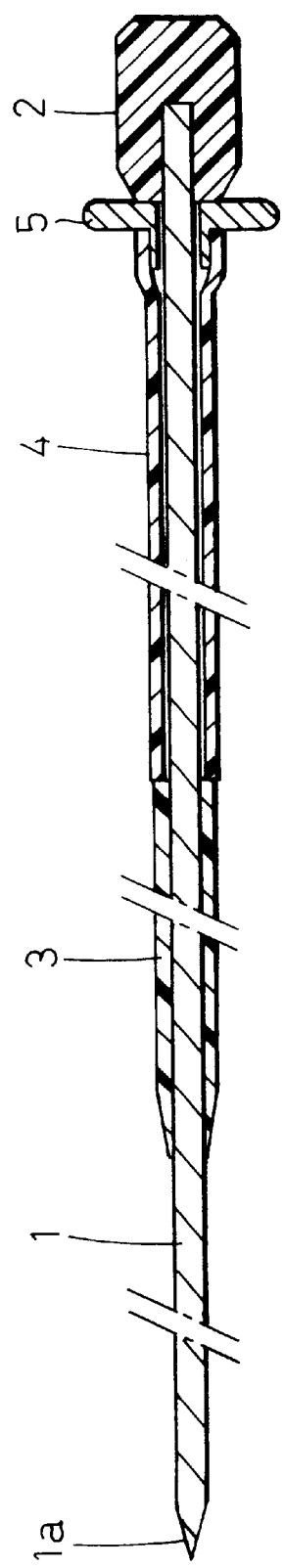
FIG. 1 is a sectional side view of a drainage tube introducer for an endoscope according to a first embodiment of the present invention.

FIG. 1 shows a drainage tube introducer for an endoscope according to a first embodiment of the present invention. A flexible guide wire 1 is a single or stranded wire of a stainless steel, for example. The overall length of the guide wire 1 is longer than the instrument-inserting channel of an endoscope used by several ten centimeters, for example.

The distal end portion 1a of the guide wire 1 is sharpened in the shape of a conical needle tip so that an organic tissue can be punctured with it. A knob 2 is secured to the proximal end of the guide wire 1. The knob 2 has a size suitable for hold with fingers.

When the guide wire 1 is a stranded wire, the strands constituting the distal end portion 1a should preferably be brazed together by silver brazing or the like. It should be noted that the distal end portion 1a of the guide wire 1 may have any shape, provided that it is sharp to a certain extent. For example, the distal end portion 1a of the guide wire 1 may be diagonally cut in the shape of a needle.

The guide wire 1 has a drainage tube 3 fitted thereon at a position closer to the distal end thereof, for example, at a distance of the order of from 1 centimeter to 10 centimeters from the distal end portion 1a.

A pusher 4 is loosely fitted on the entire length of a proximal end portion of the guide wire 1 that extends rearward from the portion on which the drainage tube 3 is held. The pusher 4 is formed from a flexible tube and adapted to push the drainage tube 3 forwardly. A flange 5 of a plastic or metallic material is secured to the proximal end of the pusher 4.

The pusher 4 is movable relative to the guide wire 1. The forward end surface of the pusher 4 abuts on the rear end surface of the drainage tube 3. Accordingly, if the pusher 4 is moved forwardly by pushing the flange 5 away from the knob 2, the drainage tube 3 can be pushed out from the distal end of the guide wire 1 by an operation conducted at the proximal end of the guide wire 1.

Figure 2:
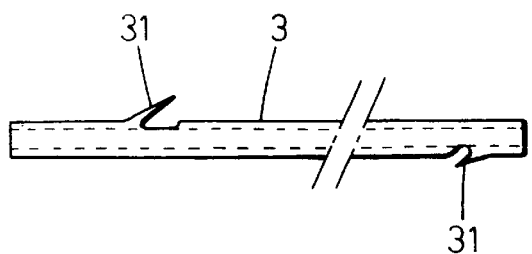
FIG. 2 is a side view of a straight drainage tube.

As the drainage tube 3, a straight drainage tube such as that shown in FIG. 2 may be used. The straight drainage tube 3 has barbs 31 to fix the straight drainage tube 3 in position in the body cavity.

Figure 3:
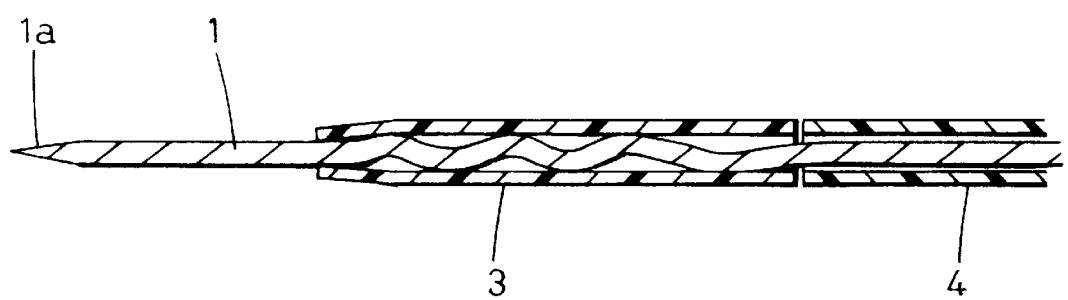
FIG. 3 is a fragmentary sectional side view showing an example of an arrangement for holding a straight drainage tube in the drainage tube introducer according to the first embodiment of the present invention.

When such a straight drainage tube 3 is used, it is preferable that, as shown in FIG. 3 by way of example, a portion of the guide wire 1 that is fitted with the drainage tube 3 is undulated so as to hold the drainage tube 3 on the guide wire 1 by frictional resistance of the drainage tube 3 to the undulated portion of the guide wire 1.

The outer surface of the distal end portion of the drainage tube 3 should preferably be tapered smoothly so that the drainage tube 3 can be smoothly pushed into a hole made in an organic tissue-by puncture.

Figure 4:
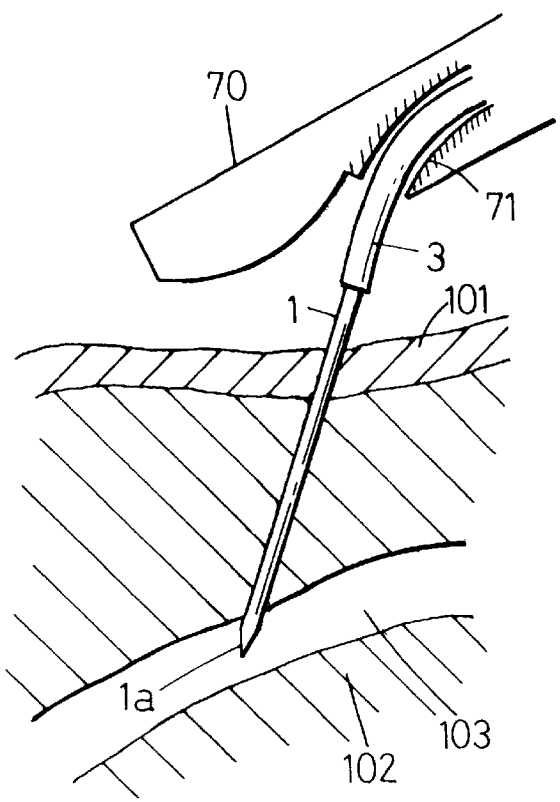
FIG. 4 is a diagram schematically showing the way in which the drainage tube introducer according to the first embodiment of the present invention is actually used.

The above-described drainage tube introducer according to the embodiment is used as follows. First, as shown in FIG. 4, the drainage tube introducer is passed through an instrument-inserting channel 71 of an ultrasonic endoscope 70. Then, the respective positions of the pancreas 102 and the pancreatic duct 103 are confirmed by jointly using optical observation and ultrasonic tomographic observation. While doing so, the operator stabs the guide wire 1 into the pancreas 102 from the stomach mucous membrane 101, aiming at the pancreatic duct 103.

Figure 5:
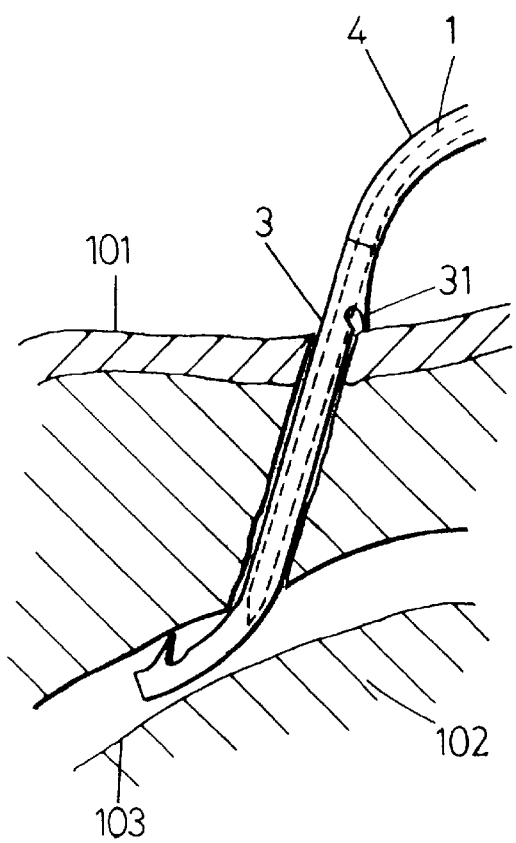
FIG. 5 is a diagram schematically showing the way in which the drainage tube introducer according to the first embodiment of the present invention is actually used.

When the distal end portion 1a of the guide wire 1 has reached a position in the pancreatic duct 103, the pusher 4 is pushed forward from the proximal end of the guide wire 1, thereby pushing the drainage tube 3 toward the distal end of the guide wire 1. When the drainage tube 3 has been positioned such that, as shown in FIG. 5, two ends thereof open into the pancreatic duct 103 and the stomach, respectively, the guide wire 1, together with the pusher 4, is drawn out of the patient's body. Consequently, the drainage tube 3 is solely left in the body cavity to draw pancreatic juice into the stomach.

Figure 6:
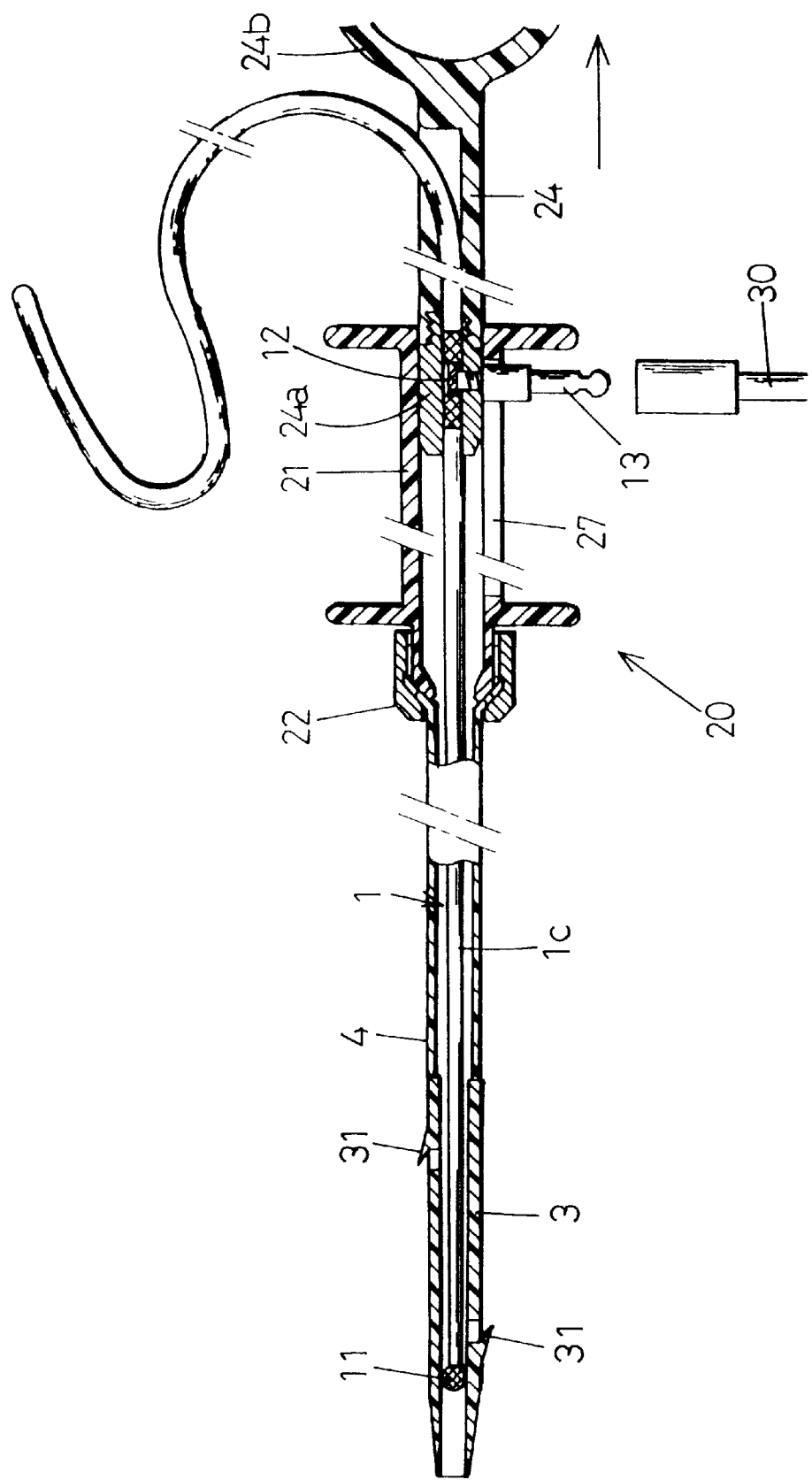
FIG. 6 is a sectional side view of a drainage tube introducer for an endoscope according to a second embodiment of the present invention.

FIG. 6 shows a drainage tube introducer for an endoscope according to a second embodiment of the present invention. In this embodiments the outer diameter of a high-frequency electrode tip 11 secured to the distal end of an electrically conductive guide wire 1 is slightly larger than the inner diameter of a drainage tube 3.

Figure 7:
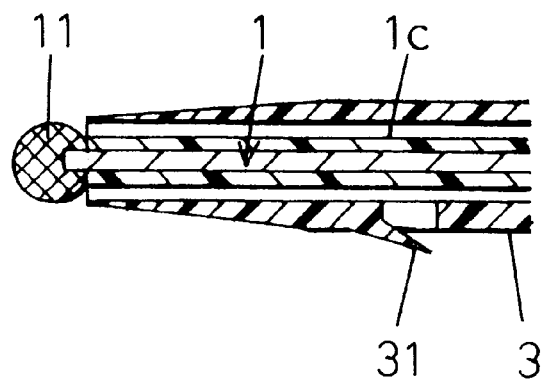
FIG. 7 is an enlarged sectional side view of a distal end portion of the drainage tube introducer according to the second embodiment of the present invention.

The drainage tube 3 is retained on the guide wire 1 by friction between the high-frequency electrode tip 11 and the drainage tube 3. FIG. 7 shows a distal end portion of the drainage tube introducer in a state where the high-frequency electrode tip 11 projects slightly from the distal end of the drainage tube 3.

The guide wire 1 is provided with an electrically insulating covering 1c over substantially the entire length thereof. The high-frequency electrode tip 11, which is made of an electrically conductive metal, is connected to the distal end of the guide wire 1 by silver brazing or soldering, for example. The high-frequency electrode tip 11 is exposed to the outside. Although the high-frequency electrode tip 11 in this embodiment has a spherical shape, various shapes are available for the high-frequency electrode tip 11.

Referring to FIG. 6, an operating part 20 is connected to the proximal (rear) end of a pusher 4. The operating part 20 has a body 21 formed from an electrically insulating plastic material. The proximal end of the pusher 4 is secured to the operating part body 21 by a retaining nut 22 screwed onto the distal end portion of the operating part body 21.

A guide wire slider 24 is slidably fitted in a through-bore provided in the axial position of the operating part body 21. A connecting member 24a is secured by thread engagement to the distal end portion of the guide wire slider 24 in the operating part body 21. The connecting member 24a is made of an electrically conductive metal.

The guide wire slider 24, exclusive of the connecting member 24a, is formed from an electrically insulating plastic material. A ring-shaped finger engagement portion 24b is formed at an end of the guide wire slider 24 projecting from the operating part body 21 so that the operator's thumb is engageable with the finger engagement portion 24b.

A connecting terminal 13 formed from an electrically conductive member is screwed into a side portion of the guide wire slider 24 to project sideways. The connecting terminal 13 is connected to a high-frequency power supply cord 30 of a high-frequency power supply (not shown) that generates an electric current for cauterization.

The guide wire 1 has a terminal receiver 12 provided at a portion thereof that is pressed from a side thereof by the distal end surface of the connecting terminal 13. The terminal receiver 12 is formed from an electrically conductive metal member. The insulating covering 1c is not provided where the terminal receiver 12 is provided.

The terminal receiver 12 is secured to the guide wire 1 by soldering or silver brazing, for example. Consequently, the terminal receiver 12 and the high-frequency electrode tip 11 are electrically connected through the guide wire 1.

The connecting terminal 13 is screwed into a metallic connecting member 24a. The connecting terminal 13 presses the terminal receiver 12 with its distal end surface, thereby securing the guide wire 1 to the connecting member 24a. Consequently, the connecting terminal 13 and the terminal receiver 12 are electrically connected to each other directly and through the connecting member 24a.

A slit 27 is formed in a side wall portion of the operating part body 21 in parallel to the axis of the operating part body 21 to allow the connecting terminal 13 to extend through and move along the slit 27. The slit 27 limits a maximum movable range in the axial direction of the guide wire slider 24.

In the drainage tube introducer arranged as stated above, the operator holds the operating part body 21 and actuates the guide wire slider 24 to move axially relative to the operating part body 21. By doing so, the high-frequency electrode tip 11 provided at the distal end of the guide wire 1 can be projected from and withdrawn into the distal end of the drainage tube 3.

If the high-frequency power supply cord 30 is connected to the connecting terminal 13, a high-frequency electric current for cauterization can be supplied to the high-frequency electrode tip 11 through the guide wire 1.

The above-described drainage tube introducer according to the embodiment is used as follows. With the distal end of the drainage tube 3 pressed against the mucous membrane surface, for example, the operating part 20 is actuated to project the guide wire 1 from the distal end of the drainage tube 3 while passing a high-frequency electric current to the pusher 4.

Consequently, organic tissues touching the high-frequency electrode tip 11 are cauterized and coagulated.

Thus, puncture can be readily performed under bleeding-free conditions. Thereafter, the drainage tube 3 is pushed out with the pusher 4 by an operation conducted at the operating part 20.

According to the present invention, an organic tissue is punctured with a guide wire through an endoscope. The guide wire has a drainage tube fitted thereon. Therefore, the drainage tube can be pushed into the punctured part directly from the guide wire. Accordingly, the procedure for introducing the drainage tube is extremely simplified. Thus, introduction of the drainage tube can be performed easily and reliably within a short period of time.

While the invention has been described by reference to specific embodiments chosen for purposes of illustration, it should be apparent that numerous modifications could be made thereto by those skilled in the art without departing from the basic concept and scope of the invention.

What is claimed is:

1. A drainage tube introducer for an endoscope comprising:
    a flexible guide wire having at a distal end thereof a puncturing portion including an electrode tip adapted to puncture an organic tissue, said electrode tip configured to be supplied with an electric current for cauterization through said guide wire;
    a drainage tube having an inner periphery fitted on a portion of said guide wire that is closer to the distal end thereof, said electrode tip having an outer periphery larger than said inner periphery of said drainage tube so that said drainage tube is held on said guide wire by frictional resistance between said electrode tip and said drainage tube; and
    a pusher loosely fitted on said guide wire axially movably so that said drainage tube is pushed out forwardly by said pusher, said pusher being formed from a flexible tube.

2. A drainage tube introducer according to claim 1, further comprising:
    an electrically insulating covering provided on a surface of said guide wire.

3. A drainage tube introducer according to claim 1, further comprising:
    an operating mechanism for conducting an operation whereby said electrode tip is projected from and withdrawn into a distal end of said drainage tube, said operating mechanism being provided at a proximal end of said pusher; and
    a connecting terminal for connection with a power supply that generates an electric current for cauterization, said connecting terminal being provided in said operating mechanism so as to connect electrically with said guide wire.

4. A drainage tube introducer according to claim 3, wherein said connecting terminal is provided such that said guide wire is locked to and unlocked from said operating mechanism by said connecting terminal.

* * * * *